US00PP24827P2

(12) United States Plant Patent
Lentjes

(10) Patent No.: US PP24,827 P2
(45) Date of Patent: Aug. 26, 2014

(54) ***LAVENDULA* 'ARMTIPP01'**

(50) Latin Name: *Lavandula angustifolia*
Varietal Denomination: Armtipp01

(71) Applicant: Gerardus Bernard Maria Lentjes, Kerkdriel (NL)

(72) Inventor: Gerardus Bernard Maria Lentjes, Kerkdriel (NL)

( * ) Notice: Subject to any disclaimer, the term of this patent is extended or adjusted under 35 U.S.C. 154(b) by 102 days.

(21) Appl. No.: 13/694,246

(22) Filed: Nov. 13, 2012

(51) Int. Cl.
*A01H 5/00* (2006.01)

(52) U.S. Cl.
USPC ..... Plt./445

(58) Field of Classification Search
USPC ..... Plt./445
See application file for complete search history.

*Primary Examiner* — Wendy C Haas
(74) *Attorney, Agent, or Firm* — Penny J. Aguirre

(57) ABSTRACT

A new cultivar of *Lavendula angustifolia*, 'Armtipp01', characterized by its vigorous rooting habit when propagated by cuttings, its gray-green foliage, its large flowers with violet petals and dark purple sepals, and its vigourous growth habit.

2 Drawing Sheets

Botanical classification: *Lavandula angustifolia.*
Variety denomination: 'Armtipp01'.

BACKGROUND OF THE INVENTION

The present invention relates to a new and distinct cultivar of *Lavandula angustifolia* and will be referred to hereafter by its cultivar name, 'Armtipp01'. 'Armtipp01' is a new variety of English lavender suitable for landscape and container use.

The new cultivar arose from an ongoing breeding program by the inventor in de Lier, The Netherlands. The Inventor made a controlled cross in October 2009 between the cultivar 'Hidcote' (not patented) as the female parent and an unnamed plant from the inventor's breeding program, designated as "nr 1402", as the male parent. 'Armtipp01' was selected as a single unique plant from the resulting seedlings in July 2010.

The new cultivar was first asexually propagated by vegetative stem cuttings by the inventor in Kerkdriel, The Netherlands in July of 2010. Asexual propagation by stem cuttings has determined that the characteristics of this cultivar are stable and are reproduced true to type in successive generations.

SUMMARY OF THE INVENTION

The following traits have been repeatedly observed and represent the characteristics of the new lavender. These attributes in combination distinguish 'Armtipp01' as a unique cultivar of lavender.

1. 'Armtipp01' has shown to have a vigorous rooting habit when propagated by cuttings.
2. 'Armtipp01' exhibits gray-green foliage.
3. 'Armtipp01' exhibits large flowers with violet petals and dark purple sepals.
4. 'Armtipp01' exhibits a vigourous growth habit.

The new cultivar of lavender can be readily distinguished from its parents and other cultivars of lavender. 'Hidcote', the female parent, differs from 'Armtipp01' in having a less vigorous rooting habit and growth habit and in having smaller flowers. The male parent, "nr 1402", differs from 'Armtipp01' in having larger flowers that are lighter in color and in having a less vigorous growth habit. 'Armtipp01' can be compared to the cultivars 'Premier' (not patented), 'Imperial Gem' (not patented), and 'Larkman Hazel' (U.S. Plant Pat. No. 20,894). All three cultivars are similar to 'Armtipp01' in having violet petals and dark purple calyxes. 'Premier' and 'Imperial Gem' differ from 'Armtipp01' in being taller in height with longer flowering stems. 'Larkman Hazel' differs from 'Armtipp01' in being of hybrid origin, in having a more compact plant habit, and in blooming in spring with some repeat bloom in fall.

BRIEF DESCRIPTION OF THE DRAWING

The accompanying colored photograph in FIG. 1 illustrates the overall appearance and distinct characteristics of the new cultivar. The photograph was taken of a one year-old plant as grown outdoors in a 17-cm container in Kerkdriel, The Netherlands. The photograph in FIG. 1 provides a side view of 'Armtipp01' in bloom.

The photograph in FIG. 2 provides a close-up view of an inflorescence of 'Armtipp01'.

Figure 1:
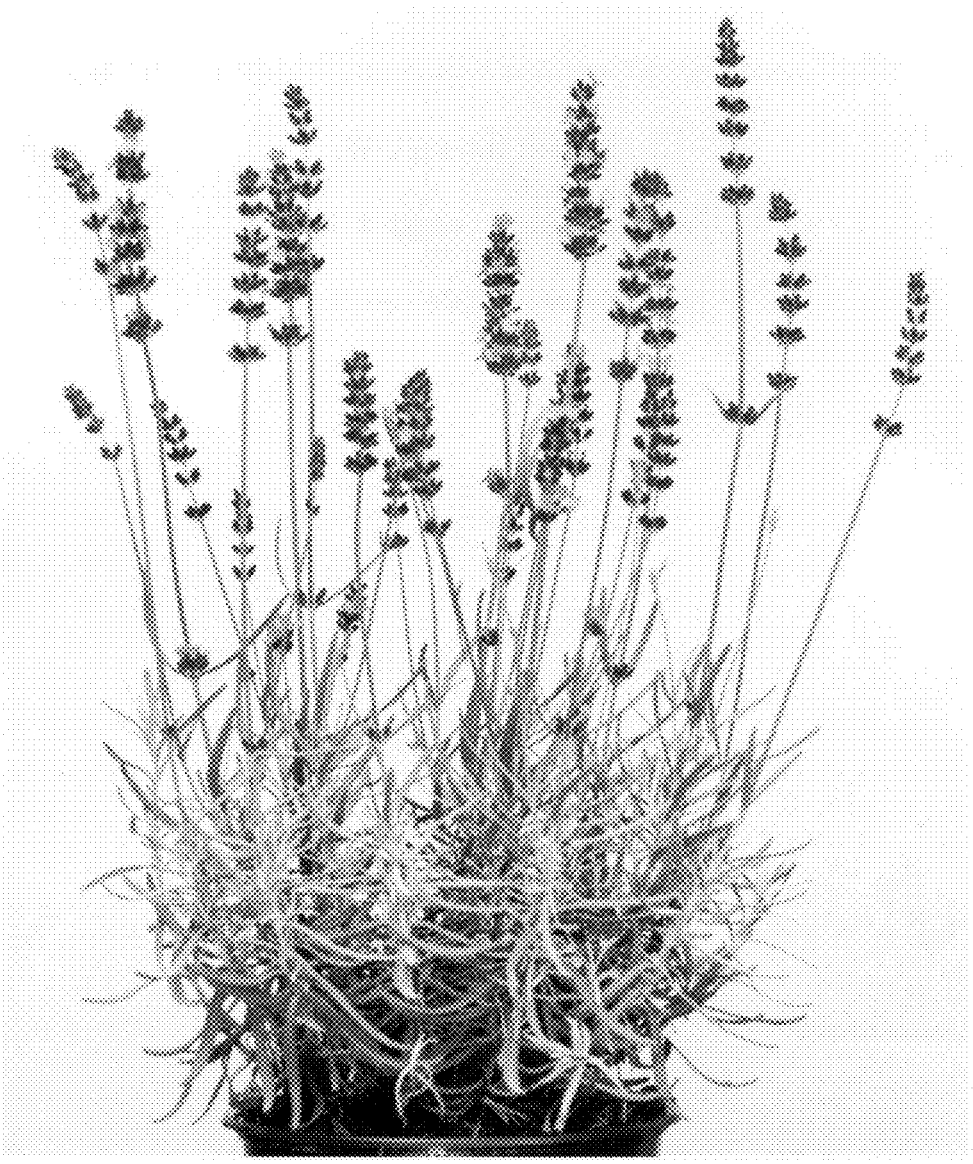
Figure 2:
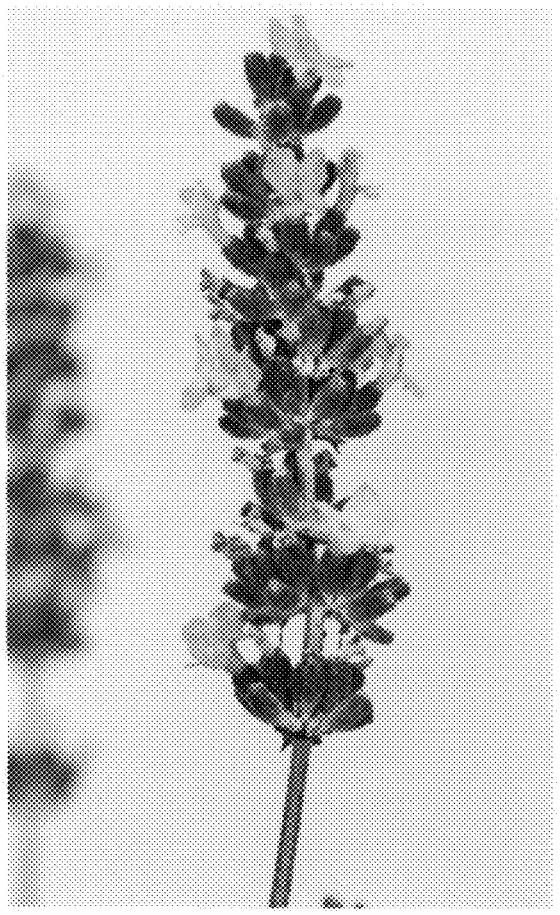
Figure 3:
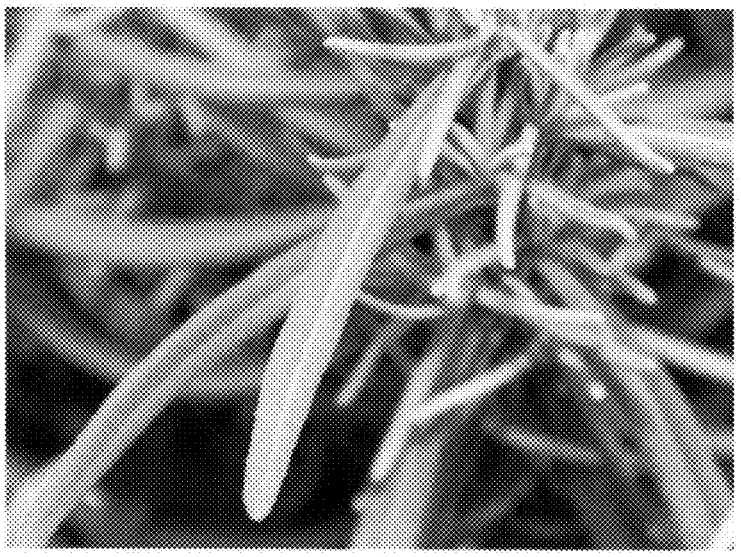

The photograph in FIG. 3 provides a close-up view of the foliage of 'Armtipp01'.

The colors in the photographs are as close as possible with the photographic and printing technology utilized. The color values cited in the detailed botanical description accurately describe the colors of the new lavender.

DETAILED BOTANICAL DESCRIPTION

The following is a detailed description of one year-old plants of the new cultivar as grown outdoors in 17-cm containers in Kerkdriel, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming habit.*—Blooms continuously from early to late summer.

*Plant type.*—Perennial, subshrub.
*Plant habit.*—Upright with upright lateral branches.
*Height and spread.*—Reaches about 40.2 cm in height and 29.9 cm in spread.
*Cold hardiness.*—At least to U.S.D.A. Zone 7b.
*Diseases and pests.*—Not more susceptible or resistant to pests and diseases than other *Lavandula.*
*Root description.*—Densely fibrous, freely branched, vigorously formed during propagation.
*Root development.*—Plants can be finished in a 12-cm container in 32 weeks from a rooted cutting.
*Propagation.*—Terminal stem cuttings.
*Growth.*—Vigourous for a *Lavendula angustifolia* cultivar.

Stem description:
*Stem shape.*—Quadangular.
*Stem color.*—Young; ranging between 13C to 137D, mature wood; 201B.
*Stem surface.*—Dull and moderately covered with woolly tomentose hairs about 0.2 mm in length and 192A in color.
*Stem size.*—Average of 15.2 cm in length and 3 mm in diameter.
*Stem strength.*—Strong.
*Stem aspect.*—Held upright.
*Branching.*—An average of 18 lateral branches on a plant developed in a 17-cm container.

Foliage description:
*Leaf shape.*—Narrowly oblong to narrowly oblanceolate to moderately revolute.
*Leaf division.*—Simple.
*Leaf base.*—Cuneate.
*Leaf apex.*—Rounded-acute.
*Leaf venation.*—Pinnate, mid rib on upper and lower surface 157C, other veins match leaf coloration.
*Leaf margins.*—Revolute.
*Leaf arrangement.*—Opposite.
*Leaf attachment.*—Sessile.
*Leaf number.*—Average of 34 (17 pairs) per lateral branch.
*Leaf surface.*—Upper surface and lower surface; moderately covered with woolly tomentose hairs about 0.2 mm in length and 192A to 192C in color.
*Leaf size.*—Average of 5 cm in length and 0.45 cm in width.
*Leaf internode length.*—Average of 9 mm in length.
*Leaf color.*—Young upper surface; 191A, young lower surface; 194A to 194B, mature upper surface; between N137C and 189A, mature lower surface; 138A.
*Leaf frangrance.*—Strongly fragrant, typical *Lavandula* scent.

Inflorescence description:
*Inflorescence type.*—Terminal verticillasters.
*Inflorescence number.*—1 per lateral stem.
*Inflorescence fragrance.*—None.
*Lastingness of inflorescence.*—Average of 10 days.
*Inflorescence size.*—Average of 7.9 cm in (height) and 2.3 cm in width.
*Flowers.*—Outward aspect, self-cleaning, salverform in shape, with one upper lip (split into two identical lobes) and one lower lip (split into three identical lobes), lobes are identical in shape, but lobes of lower lip are smaller, average of 60 flowers per inflorescence, about 0.8 mm in depth (height) and 7 mm in diameter.
*Flower buds.*—Average of 5 mm in length and 2.5 mm in diameter, elliptic to oblong in shape, color is 145B, entire surface is densely covered in a woolly pubescence to small to be measured and N89A to N89B color.
*Petals.*—Dull and smooth on upper and lower surfaces, rotate in arrangement, 2 (upper lip split in 2 lobes, lower lip split in 3 lobes; all lobes are identical in shape and colour), spathulate in shape, lower 70% of petals are fused into tube, entire margin, upper part of petal apex split into two lobes, lower petal apex split into three lobes, apexes are rounded, length of upper lip is 12 mm, length of lower lip is 11 mm, width of upper lip is 6 mm, width of lower lip is 7 mm, color: upper and lower surface of petal when opening; a blend of N87A and N88A with tube slightly lighter; N87B to N87C, upper and lower surface when fully open; a blend of N87C and N88C, tube is slightly lighter; N87B to N87C.
*Sepals.*—Linear in shape and fused into tube, entire magin, broadly acute apex, fused base, 6 mm in length and 0.5 mm in width, immature upper and lower surfaces are smooth and 145B in color, mature upper and lower surfaces are 145B in color and very densely covered with woolly pubescence too small to measure and N89A to N89B in color.
*Calyx.*—Closed campanulate in shape, 5 mm in length and 3 mm in diameter.
*Peduncles.*—Strong, average of 20.9 cm in length and 2 mm in diameter, held at an average angle of 0° (straight on top of lateral branch), between 13C and 137D and moderately covered with woolly tomentose hairs about 0.2 mm in length and 192A in color.
*Pedicels.*—Moderately strong, average of 1 mm in length and 1 mm in diameter, average angle of 50° (0°=straight upright) and 145D in color.
*Bracts.*—Fertile, broadly rhomboidal in shape, entire margins, cuspidate apex, cuneate base, average of 5 mm in length and 5 mm in width, 199C to 199D in color with veins 200B in color.

Reproductive organs:
*Pistils.*—1, pistil is 7 mm in length, stigma is narrow, club-shaped and N88D in color, style is 6 mm in length and 156D in color, ovary is 146A in color.
*Stamens.*—4, anthers are dorsifixed, kidney-shaped, about 0.5 mm in length and 197A to 197B in color, the filament is implanted in petal and 1 mm in length, pollen is moderate in quantity and 23A in color.
*Fruit and seeds.*—No fruit or seed development has been observed.

It is claimed:

1. A new and distinct cultivar of *Lavendula* plant named 'Armtipp01' as herein illustrated and described.

* * * * *